United States Patent
Aszodi et al.

(10) Patent No.: US 10,308,683 B2
(45) Date of Patent: Jun. 4, 2019

(54) BICYCLIC LIPOLANTIPEPTIDE, PREPARATION AND USE AS ANTIMICROBIAL AGENT

(71) Applicant: DEINOVE, Grabels (FR)

(72) Inventors: Josef Aszodi, Pontault-Combault (FR); Denis Carniato, Marcoussis (FR); Dominique Le Beller, Jaux (FR); Guillaume Lesquame, Bailleul (FR); Marie-Helene Quernin, Marcq en Baroeul (FR)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 15/740,822

(22) PCT Filed: Jul. 1, 2016

(86) PCT No.: PCT/EP2016/065568
§ 371 (c)(1),
(2) Date: Dec. 29, 2017

(87) PCT Pub. No.: WO2017/001678
PCT Pub. Date: Jan. 5, 2017

(65) Prior Publication Data
US 2018/0201646 A1 Jul. 19, 2018

(30) Foreign Application Priority Data

Jul. 1, 2015 (EP) .................................... 15306065
Oct. 30, 2015 (EP) .................................... 15192409

(51) Int. Cl.
*A61K 38/12* (2006.01)
*C07K 7/06* (2006.01)
*A61K 38/00* (2006.01)
*C07K 7/50* (2006.01)
*C07K 7/56* (2006.01)
*A01N 43/90* (2006.01)
*C12R 1/00* (2006.01)
*A01N 47/44* (2006.01)

(52) U.S. Cl.
CPC ................ *C07K 7/06* (2013.01); *A01N 43/90* (2013.01); *A01N 47/44* (2013.01); *A61K 38/00* (2013.01); *C07K 7/50* (2013.01); *C07K 7/56* (2013.01); *C12R 1/00* (2013.01)

(58) Field of Classification Search
None
See application file for complete search history.

(56) References Cited

FOREIGN PATENT DOCUMENTS

EP 1 788 074 5/2007

OTHER PUBLICATIONS

Smyth, Handbook of Hydrocarbon and Lipid Microbiology, Springer-Verlag Berlin Heidelberg, 2010, 3689-3704 (Year: 2010).*
Kwok, Y. et al. "Rapid isolation and characterization of bacterial lipopeptides using liquid chromatography and mass spectrometry analysis" Proteomics, Jul. 1, 2011, pp. 2620-2627, vol. 11, No. 13.
Smyth, T. J. P. et al. "Isolation and Analysis of Lipopeptides and High Molecular Weight Biosurfactants" Handbook of Hydrocarbon and Lipid Microbiology, Jan. 1, 2010, pp. 3687-3704, Chapter 27, K. N. Timmis (ed.), Springer-Verlag.
Written Opinion in International Application No. PCT/EP2016/065568, dated Aug. 4, 2016, pp. 1-6.

* cited by examiner

*Primary Examiner* — Satyanarayana R Gudibande
(74) *Attorney, Agent, or Firm* — Saliwanchik, Lloyd & Eisenschenk

(57) ABSTRACT

The invention relates to a new bicyclic lipolantipeptide, representing a new class of lantipeptide, and salts thereof, their preparation from a culture of a *Microbacterium arborescens*, and their use as antimicrobial agent in the prevention and treatment of infections in humans, animals or plants.

8 Claims, 18 Drawing Sheets

BICYCLIC LIPOLANTIPEPTIDE, PREPARATION AND USE AS ANTIMICROBIAL AGENT

CROSS-REFERENCE TO RELATED APPLICATION

This application is the U.S. national stage application of International Patent Application No. PCT/EP2016/065568, filed Jul. 1, 2016.

BACKGROUND OF THE INVENTION

Antimicrobial resistance, which entails the microorganisms ability to find ways aimed at circumventing the actions of the drugs used to cure the infections caused by such microorganisms, is held as a current public health issue not only because of the growing trend of resistant bacteria, but also due to the lack of new antibiotics.

Thus, there is a growing demand of antibiotics not only due to the resistance issue, but also to the extended life expectancy of the population.

For example, multi-drug resistant Gram-positive bacteria (MDRGP) still continue to pose challenges to the scientific community, which involve *Staphylococcus aureus*, whose first penicillin-resistant strains emerged more than fifty years ago. Also, the multiple-drug resistant Gram-negative bacteria (MDRGN) have turned into an issue of concern, particularly, the *E. coli*-resistant strains.

Therefore, the search for new chemical entities with antimicrobial properties and structures differing from those found in conventional antibiotics is viewed as a pressing need to develop new ways to curb these resistant infections. The applicant has found that *Microbacterium* is particularly useful to produce novel compounds having antibacterial activity. All *Microbacterium* strains described in the literature so far have been isolated from environmental sources. Clinical microbiology diagnostic laboratory receives almost any clinical specimen, including swabs, feces, urine, blood, sputum, cerebrospinal fluid, synovial fluid, as well as possible infected tissue. However, over nearly two decades *Microbacterium* strains have been isolated from clinical specimens. Initially, these yellow- or orange-pigmented, fermentative gram-positive rods (GPRs) were identified as CDC coryneform group A-4 and A-5 bacteria, but further investigations revealed that they belong to the genus *Microbacterium* (Primary Identification of *Microbacterium* spp. Encountered in Clinical Specimens as CDC Coryneform Group A-4 and A-5 Bacteria, Guido FUNKE, JOURNAL OF CLINICAL MICROBIOLOGY, January 1995, p. 188-192).

BRIEF SUMMARY OF THE INVENTION

We have shown that the genome of *Microbacterium* codes for enzymatic pathways producing biologically active secondary metabolites. The present invention provides new compounds having antibacterial activity isolated from a microorganism of the genus *Microbacterium*, more particularly the strain *Microbacterium arborescens* CIP 55.81T (Collection Institut Pasteur).

SUMMARY OF THE INVENTION

Figure 1:
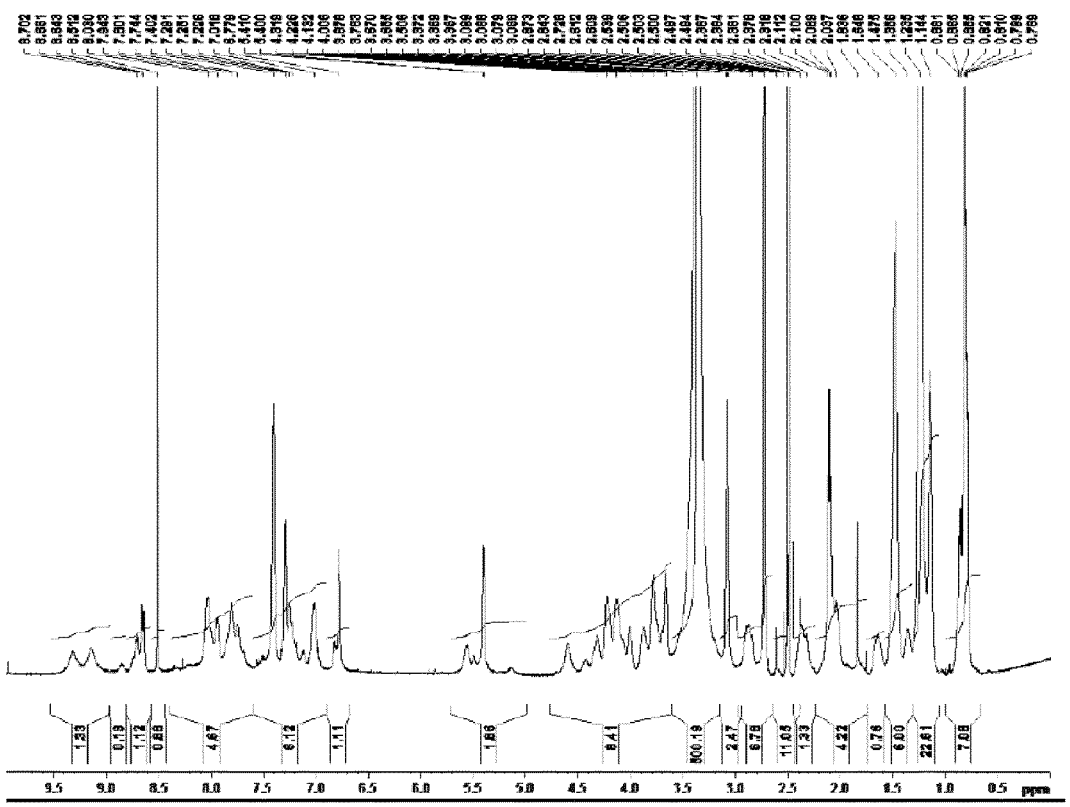
FIG. 1 displays the 1H NMR spectrum of compound MH+=979.57340 (600 MHz, DMSO-d6, 300K) Full spectrum.
Figure 2:
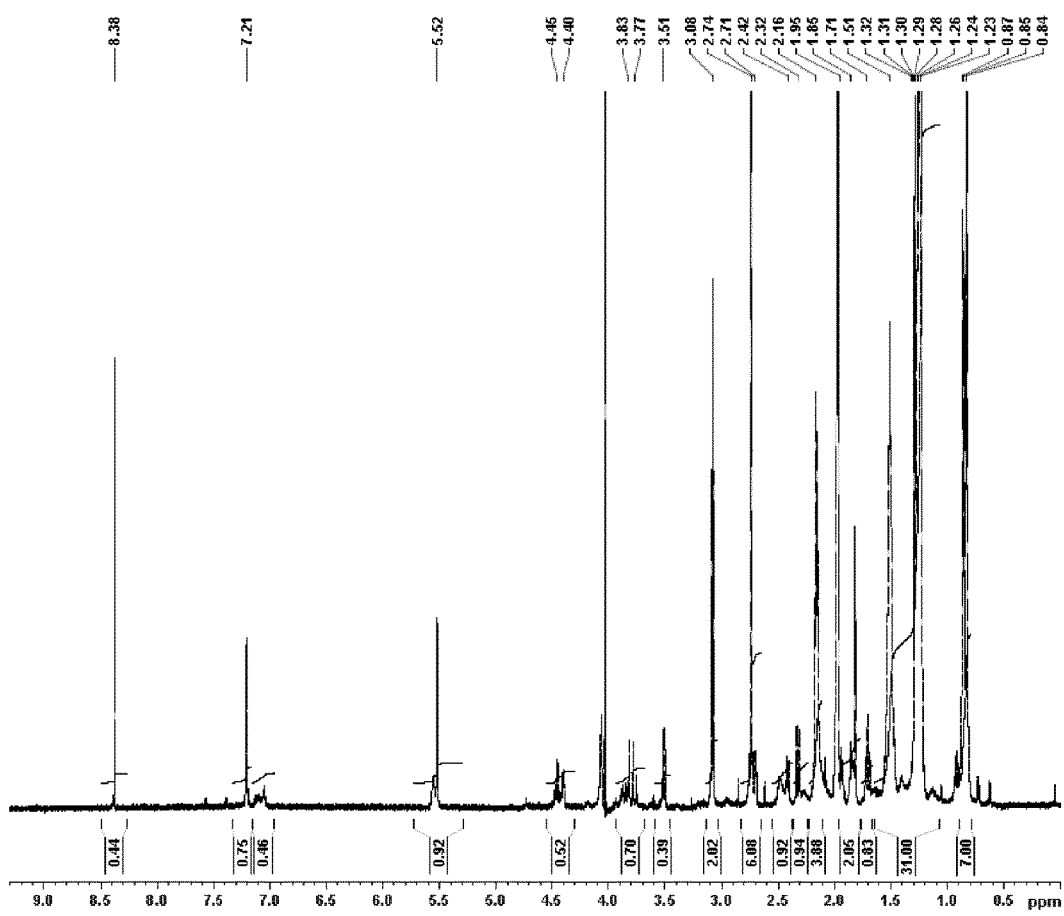
FIG. 2 displays the 1H NMR spectrum of compound MH+=979.57340 (600 MHz, CD3CN/D2O, 300K) Full spectrum.
Figure 3:
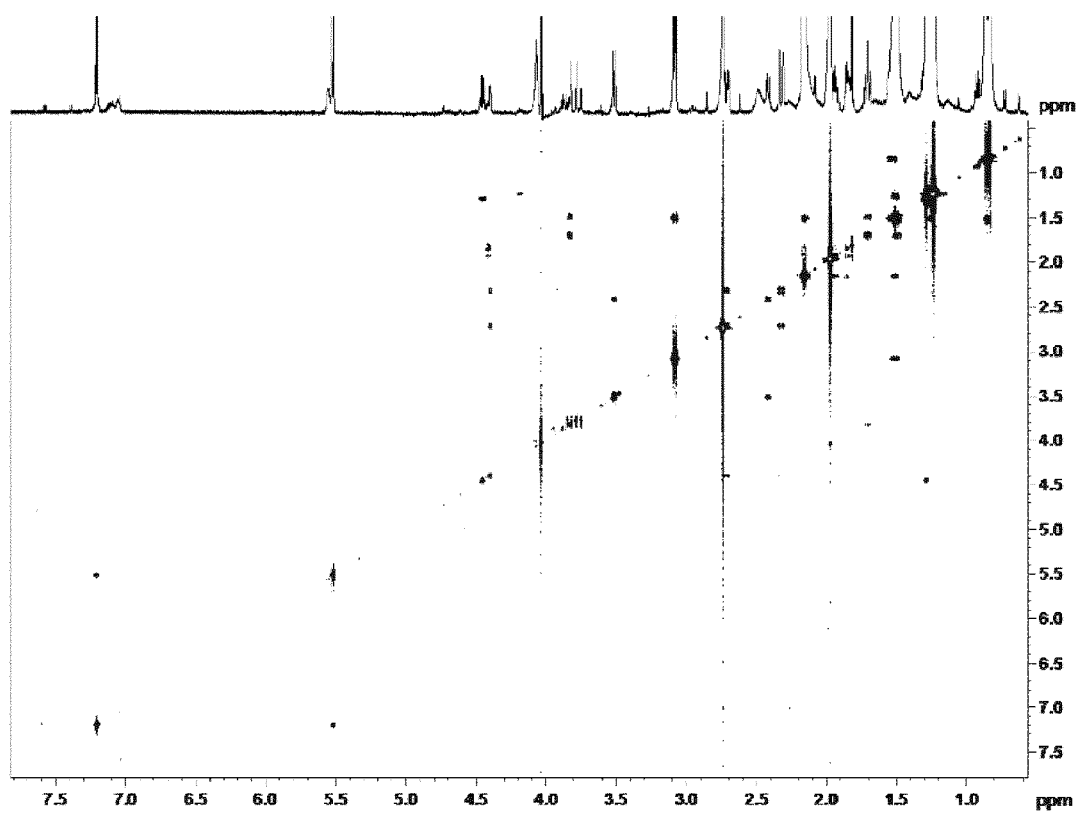
FIG. 3 displays the $^1$H-$^1$H COSY NMR spectrum of compound MH$^+$=979.57340 (600 MHz, CD$_3$CN/D$_2$O, 300K).
Figure 4:
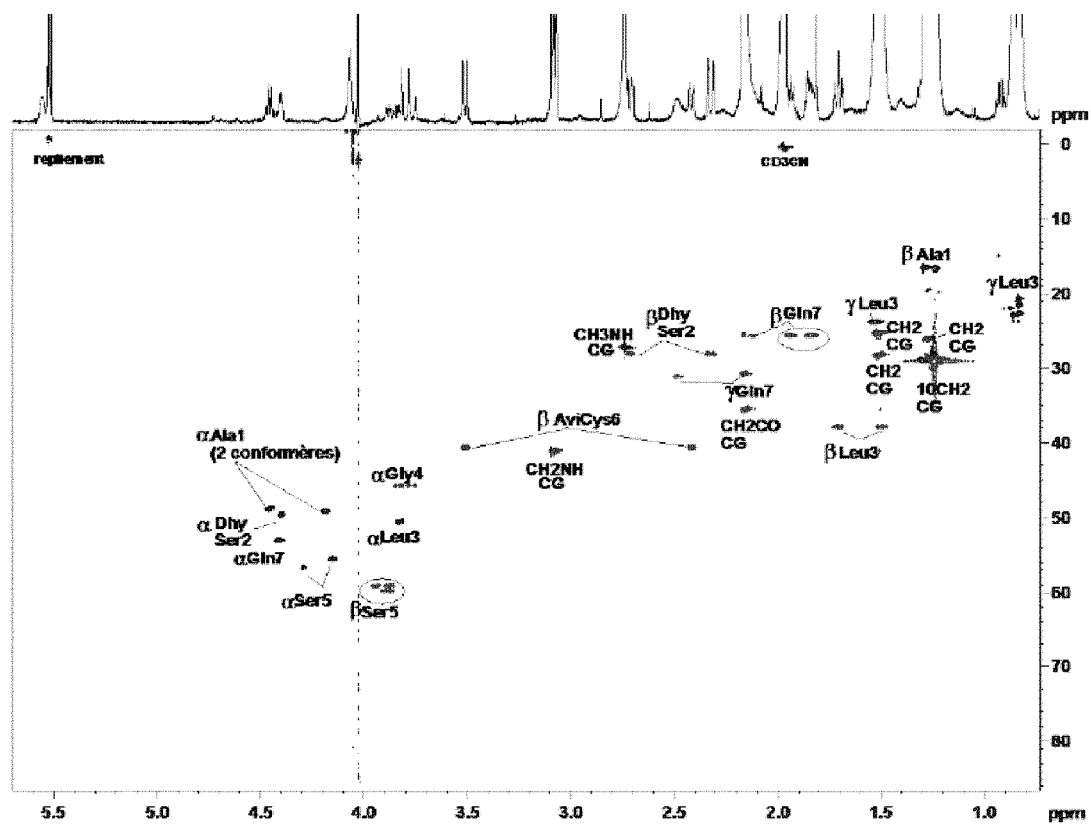
FIG. 4 displays the C-edited HSQC spectrum (from 0.0 to 5.5 ppm) of compound MH$^+$=979.57340 (600 MHz, CD$_3$CN/D$_2$O, 300K).
Figure 5:
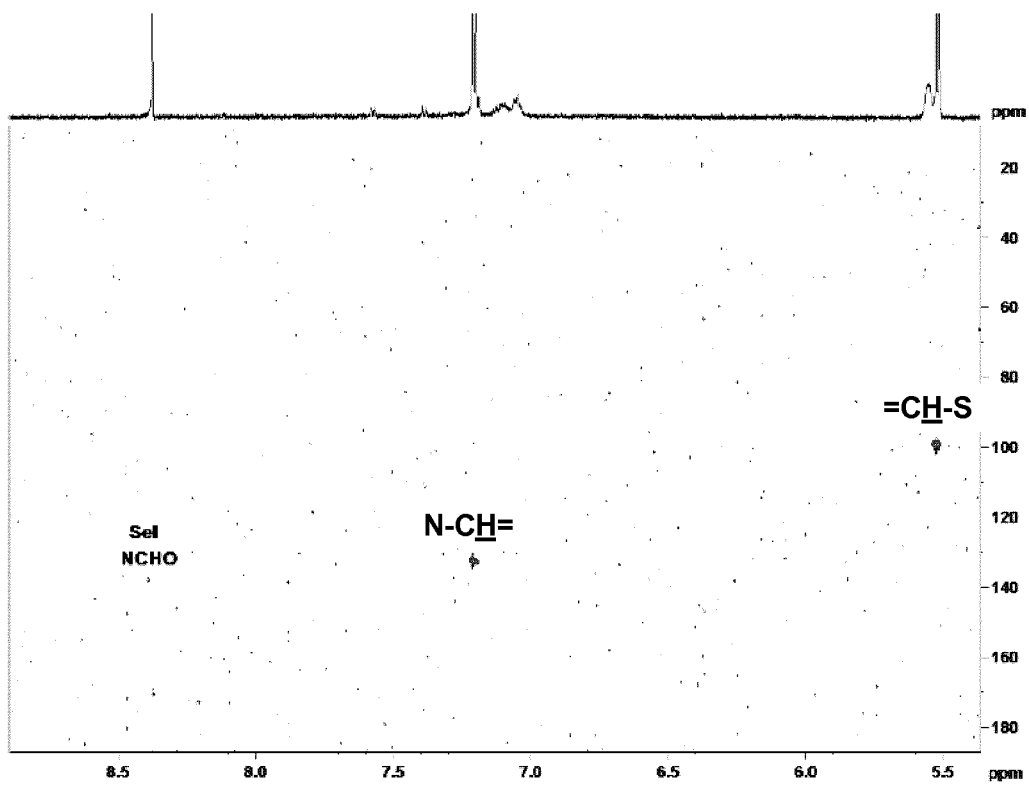
FIG. 5 displays the C-edited HSQC spectrum (from 5.5 to 10 ppm) of compound MH$^+$=979.57340 (600 MHz, CD3CN/D2O, 300K) containing the aminovinylthio group.
Figure 6:
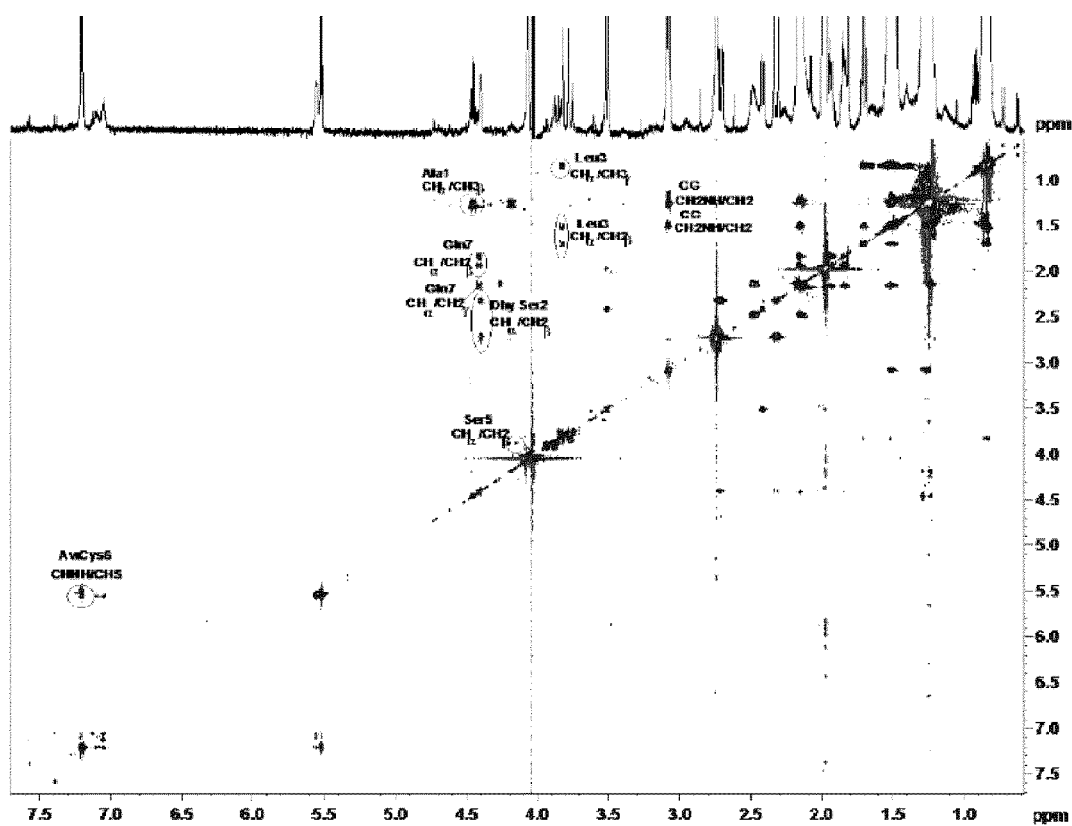
FIG. 6 displays the TOCSY spectrum of compound MH+=979.57340 (600 MHz, CD3CN/D2O, 300K).
Figure 7:
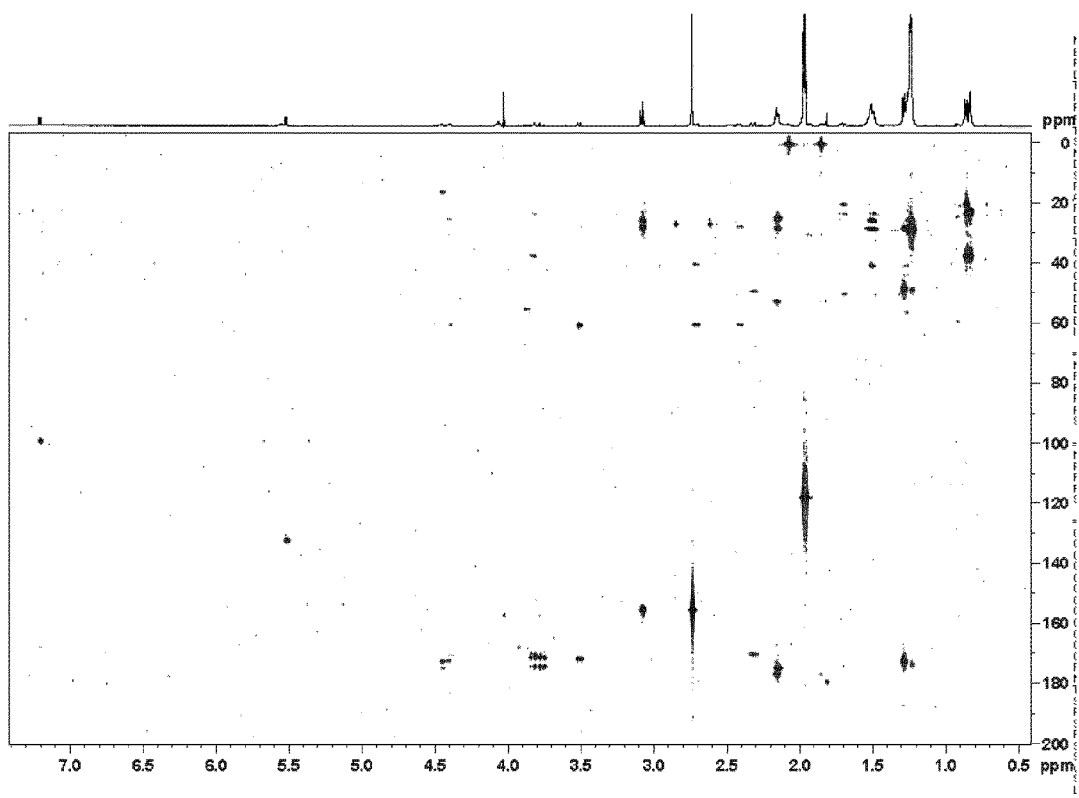
FIG. 7 displays the HMBC NMR spectrum of compound MH$^+$=979.57340 (600 MHz, CD$_3$CN/D$_2$O, 300K).
Figure 8:
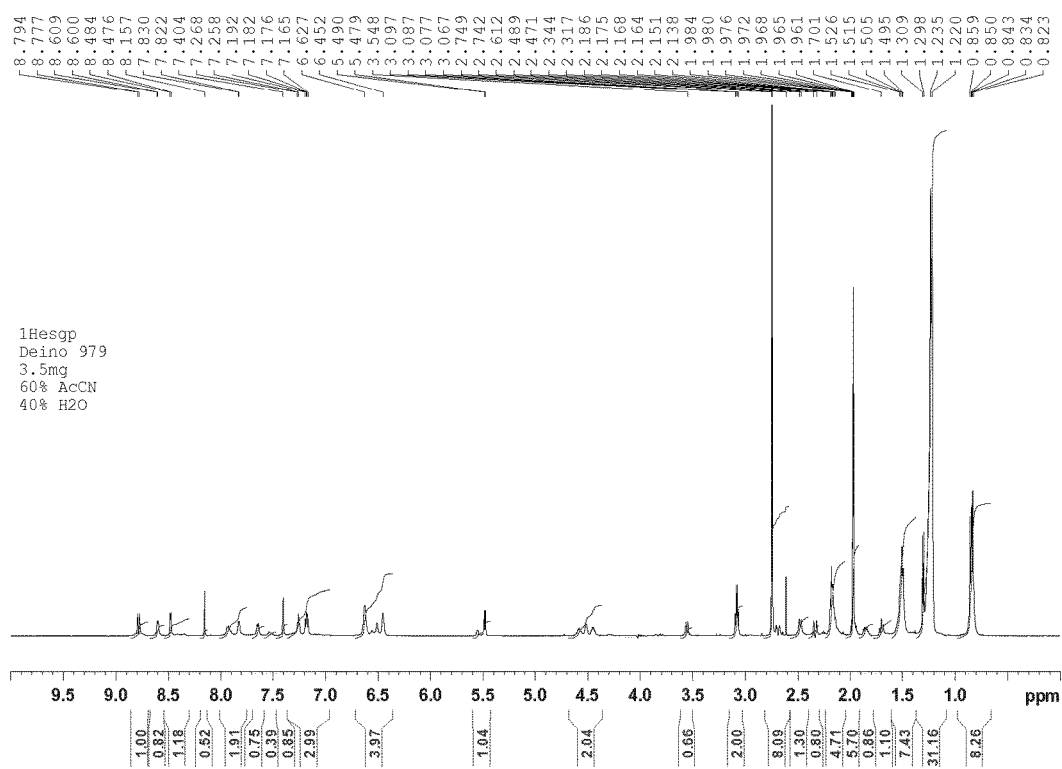
FIG. 8 displays the $^1$H NMR spectrum of compound MH$^+$=979.57340 (700 MHz, CD$_3$CN/D$_2$O: 3/2 with 0.2% CD3COOD, 305K).

Lantipeptides are ribosomally synthesized post-translationally modified natural products falling into 4 classes, (Nat Prod Rep. 2013 Jan. 30(1), 108-160 DOI: 10.1039/c2np20085f) some but not all of them displaying antimicrobial activity.

The invention relates to bicyclic compounds representing a new class of lantipeptides comprising at least (i) the following amino acids: Ala, Gln, Leu and Ser, each being of the L-configuration, and Gly, (ii) an aminovinylthio group, and (iii) a substituent consisting of a linear fatty acid chain, in particular $C_{15}$ or $C_{17}$, which may contain a carbon-carbon double bond, the terminal carbon of the fatty chain carrying a guanidine group optionally substituted by one or two ($C_1$-$C_6$) alkyl groups, and their acid salts. The new compounds can be classified as lantipeptides based on the biosynthetic pathway even if they have a much smaller molecular weight, and the presence of a fatty acid substituent is a unique feature in lantipeptides, therefore they have been referred to as lipolantipeptides.

The invention relates in particular to a bicyclic lipolantipeptide as described above, in which the guanidine group is substituted by two methyl groups, carried by the two terminal nitrogen atoms.

The lipolantipeptide according to the invention can take the form of a mixture of several compounds defined as above, in particular of three compounds (hereafter designated as A, B and C) that differ at the level of the fatty chain structure, namely it is a saturated $C_{15}$ chain or a saturated or unsaturated $C_{17}$ chain, the latter may contain one unsaturation as defined hereafter. Each of the compounds A, B and C in itself constitutes an object of the invention. The molecular weights and molecular formulae of the compounds in question are respectively 978 and $C_{45}H_{78}N_{12}O_{10}S$, 1006 and $C_{47}H_{82}N_{12}O_{10}S$, and 1004 and $C_{47}H_{80}N_{12}O_{10}S$ (hereafter respectively compounds A, C and B).

The lipolantipeptide according to the invention is furthermore characterized in that:

i) HR MS/MS fragmentation shows two peaks characteristics of the substituted guanidines, a loss of mass of 31.0427 and 70.0538 corresponding to a loss of groups $CH_3NH_2$ and $CH_3N=C=NCH_3$ respectively;

ii) the 1H NMR chemical shifts in $CD_3CN/H_2O$ of the two vinylic protons of the aminovinylthio group are at 5.5 and 7.2 ppm.

A representation of compounds A, B and C is given hereafter.

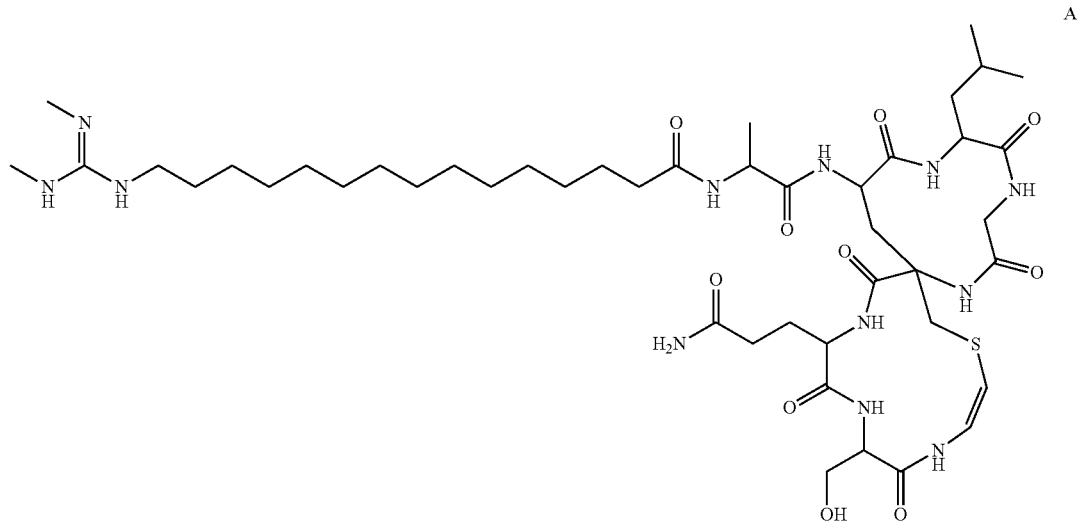

A

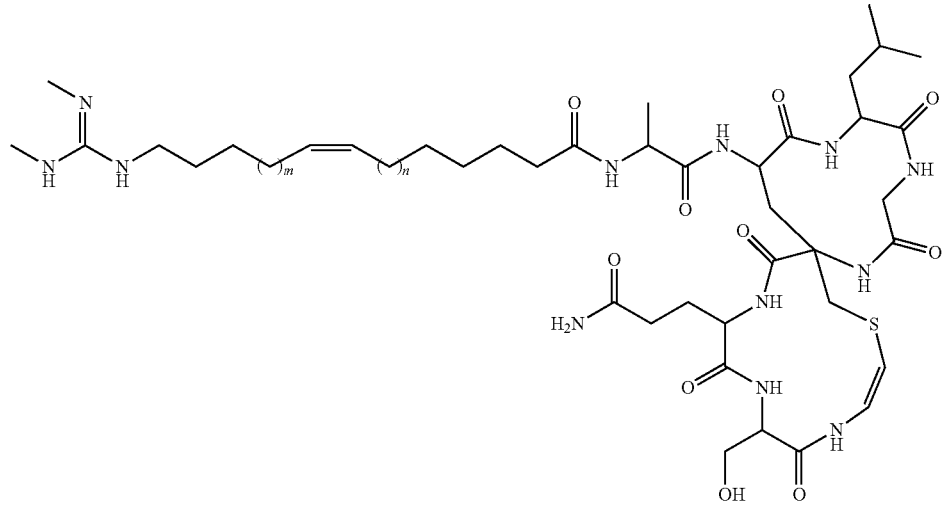

B ( ) m and ( ) n representing a total of 7 CH$_2$.

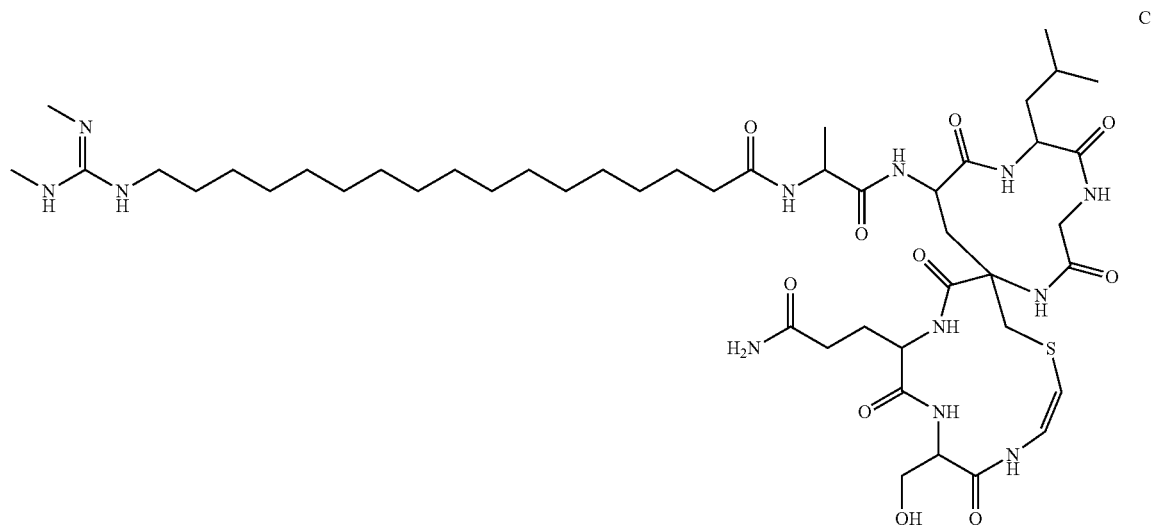 [SMILES: C/N=C(\NC)NCCCCCCCCCCCCCCCCC(=O)NC(C)C(=O)NC1CC2(CS/C=C\NC(=O)C(CO)NC(=O)C(CCC(N)=O)NC2=O)NC(=O)CNC(=O)C(CC(C)C)NC1=O]

C

The lipolantipeptide according to the invention is endowed with antimicrobial properties which make it useful as an antimicrobial agent for the prevention and therapeutical treatment of infections due to microbial pathogens in humans, animals and also vegetals and this constitutes a further object of the invention.

The lipolantipeptide according to the invention is especially useful as antibacterial against Gram-positive bacteria growing under aerobic or anaerobic conditions. Such drugs are useful against bacteria of the genus *Staphylococcus*, more specifically *S. aureus* and coagulase-negative staphylococci like *S. epidermidis* and *S. saprophyticus* (including multiresistant strains such as methicillin-resistant staphylococci, vancomycin-intermediate and vancomycin-resistant *Staphylococcus aureus*), *Enterococcus* (including *E. faecium* and including vancomycin-resistant isolates), *Streptococcus* (including *S. pneumoniae*, penicillin-resistant *S. pneumoniae*, *S. agalactiae*, *S. pyogenes*, and streptococci of the *viridans* group), *Clostridium difficile*, *Propionibacterium acnes*.

Besides, it also demonstrates antimycobacterial activity against *Mycobacterium tuberculosis*, a major infection of concern in humans including patients with acquired immunodeficiency syndrome.

In addition to the above described uses, the lipolantipeptide according to the invention can also be used in the crop protection against plant pathogens. One can mention for example control of *Phytophthora* blight infection caused by *Phytophthora* in red pepper.

The invention also relates to pharmaceutical compositions comprising, as active principle, a therapeutically effective amount of at least one lipolantipeptide according to the invention. In the compositions of the invention, the active principle can be in association with a pharmaceutically acceptable carrier or excipient.

The pharmaceutical compositions according to the invention are advantageously formulated to be administered under oral, topical, transdermal, sub-lingual, rectal, parenteral including intravenous, intramuscular, intraperitoneal and sub-cutaneous routes, with individual doses appropriate for the patient to be treated.

The preferred routes are transdermal routes.

The compositions according to the invention can be solid, liquid including solutions, emulsions or suspensions, or in the form of a gel/cream and be presented in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives. These compositions can in particular be presented in the form of a powder intended to be dissolved or suspended extemporaneously in an appropriate vehicle, for example, non-pyrogenic sterile water.

The dose of the lipolantipeptide according to the invention administered varies according to the condition to be treated, the patient in question and the administration route. It can, for example, be comprised between 10 μg and 10 g per day for an adult.

EXPERIMENTAL PART

In the following, the present invention is specifically described by way of examples but the present invention is not limited to only these.

Preparation of Culture Medium for Production of Lipolantipeptide

YPG (Peptone, Glucose, Yeast Extract) Medium

The composition of the YPG medium is as follows: glucose, 1 g/L; peptone, 10 g/L; yeast extract, 5 g/L; MOPS (3-(N-morpholino)propansulfonic acid) 150 mM The 10% glucose, 2M MOPS and 3M KOH solutions are prepared separately.

The 10% Glucose (100 ml)
10 g of powder, distilled water qsp 100 mL
sterilization at 110° C. for 30 minutes
3M KOH
MM=56.11 g/mol
Purity: 85%
56.11*0.85=47.6 g/mol
Weigh 143.08 g of powder for a qsp of 1 L with distilled water
Autoclave at 121° C. for 20 minutes
2M MOPS (1 L)
MM=209.26 g/mol
Weigh 418.52 g of powder for a qsp of 920 mL
Filter on 0.22 microns under sterile conditions
Add 80 mL of sterile 3M KOH
YPGYPG Medium
10 g/L of peptone
5 g/L yeast extract
Sterilization at 121° C. for 20 minutes
Addition of sterile 10% glucose: final concentration 0.1% (final concentration 1 g/L)
Addition of sterile MOPS (final concentration 150 mM)
Adjust pH to 7.2 using sterile KOH or sterile KCl depending on the initial pH.
Culture of *Microbacterium arborescens* CIP 55.81T.
Pre-Culture (P1)
A 500 ml flask containing as final volume 100 ml YPG medium was inoculated with a colony of the primary *Microbacterium arborescens* strain bank and incubated at 30° C. for 24 h with stirring at 160 rotations per minute (rpm). Optical density (OD) at 600 nm was then measured by a spectrophotometer until the *Microbacterium arborescens* strain was at the beginning/middle of its exponential growth phase (1<OD at 600 nm<3)

The purity of the pre-culture was monitored by seeding on YPG agar. The plates were incubated at 30° C. for 48 h.

Cultures in Erlenmeyer Flasks

A 5000 ml flask, containing as a final volume 1000 ml YPG medium was inoculated with the 100 ml of pre-culture (P1) and incubated at 30° C. for 96 hours with stirring at 160 rpm. Initial OD at 600 nm ranged between 0.1 and 0.3.

Purity of fermentation was monitored at the end of 96 hours by seeding a YPG agar. The plates were incubated at 30° C. for 48 h.

The culture was centrifuged to 10,000 g for 45 min at 25° C.

The supernatant was recovered and kept at 4° C.

Extraction of Lipolantipeptide

Extraction of the compounds having antimicrobial activity from the supernatant was carried out by liquid-liquid extraction in contact with a mixture of dichloromethane/methanol in a 80:20 ratio. The operation is carried out 5 times using the collected supernatant. The solvent was concentrated to a final volume of 20 ml in a rotary evaporator at 50° C., 7 mbar, 160 rpm. A precipitate was formed, the supernatant was taken off and the precipitate (brown) (PRE1) was redissolved in methanol and the solvent was evaporated under vacuum.

PRE1 was washed several times with dichloromethane then with dichloromethane/Methanol (99/1) to obtain precipitate 2 (yellow) (PRE2).

Purification by Preparative HPLC

PRE2 was purified by taking 150 mg in a mixture of DMSO, $H_2O$, acetonitrile 1/1/1 (v/v/v). The sample was manually loaded (1.5 mL) into the injection system of the semi-preparative HPLC manufactured by Waters. The column used was a C18 (5 microns, 150×21 mm, Gemini, Phenomenex). Elution was performed at a flow rate of 15 mL/min according to the gradient shown in Table 1 below:

TABLE 1

Elution as a function of respective concentrations of buffers A and B

| Time (min) | Buffer A ($H_2O$) | Buffer B (Acetonitrile + 0.1% formic acid) |
|---|---|---|
| 0 | 100 | 0 |
| 2 | 100 | 0 |
| 17 | 50 | 50 |
| 19 | 0 | 100 |
| 23 | 0 | 100 |
| 25 | 100 | 0 |
| 30 | 100 | 0 |

The three peaks corresponding to compounds A, B and C were collected at 15.1 min, 15.8 min and 16.3 min respectively.

The obtained compounds were analyzed by MALDI-TOF mass spectrometry and by NMR. The used conditions appear hereafter in the attached figures.

Figure 9:
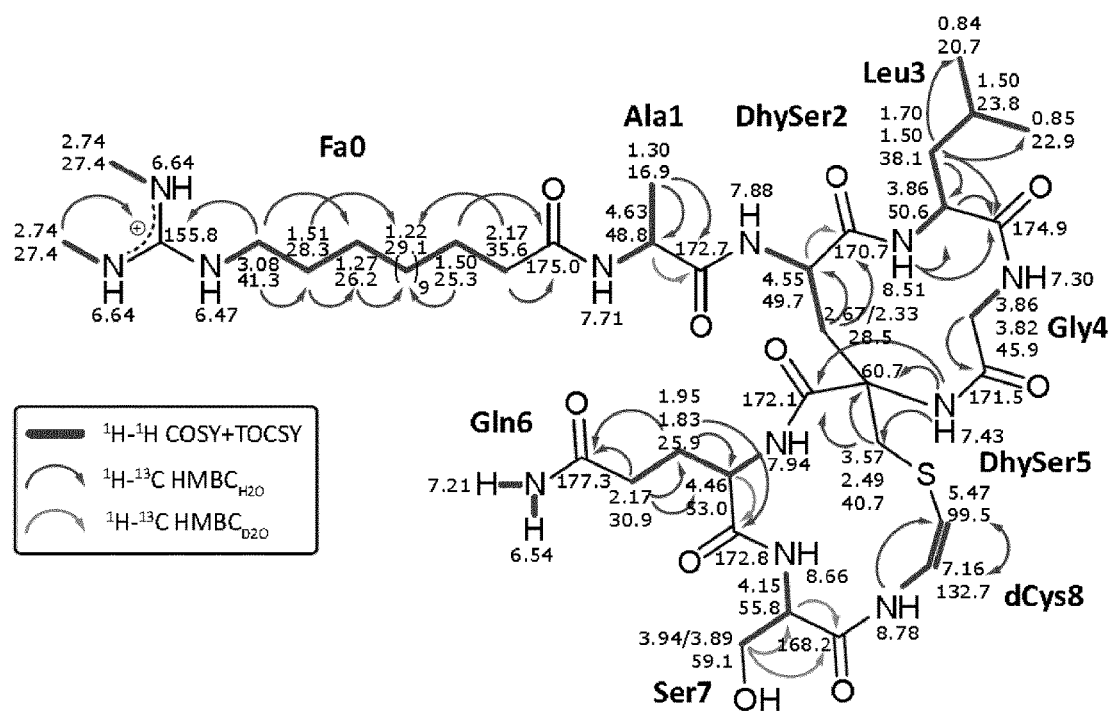
FIG. 9 displays the intra-residual NMR assignment of compound MH$^+$=979.57340.

The chemical shift assignment and all observed intra-residual connectivities are summarized in table 4 and FIG. 9 respectively. For the vinylic protons of the aminovinylthio group, a $^3J_{H\alpha H\beta}$ coupling constant of 7.3 Hz, clearly indicating a cis-isomer, was observed.

In FIG. 9 the intra-residual NMR assignment of compound MH+=979.57340 is given.

Figure 18:
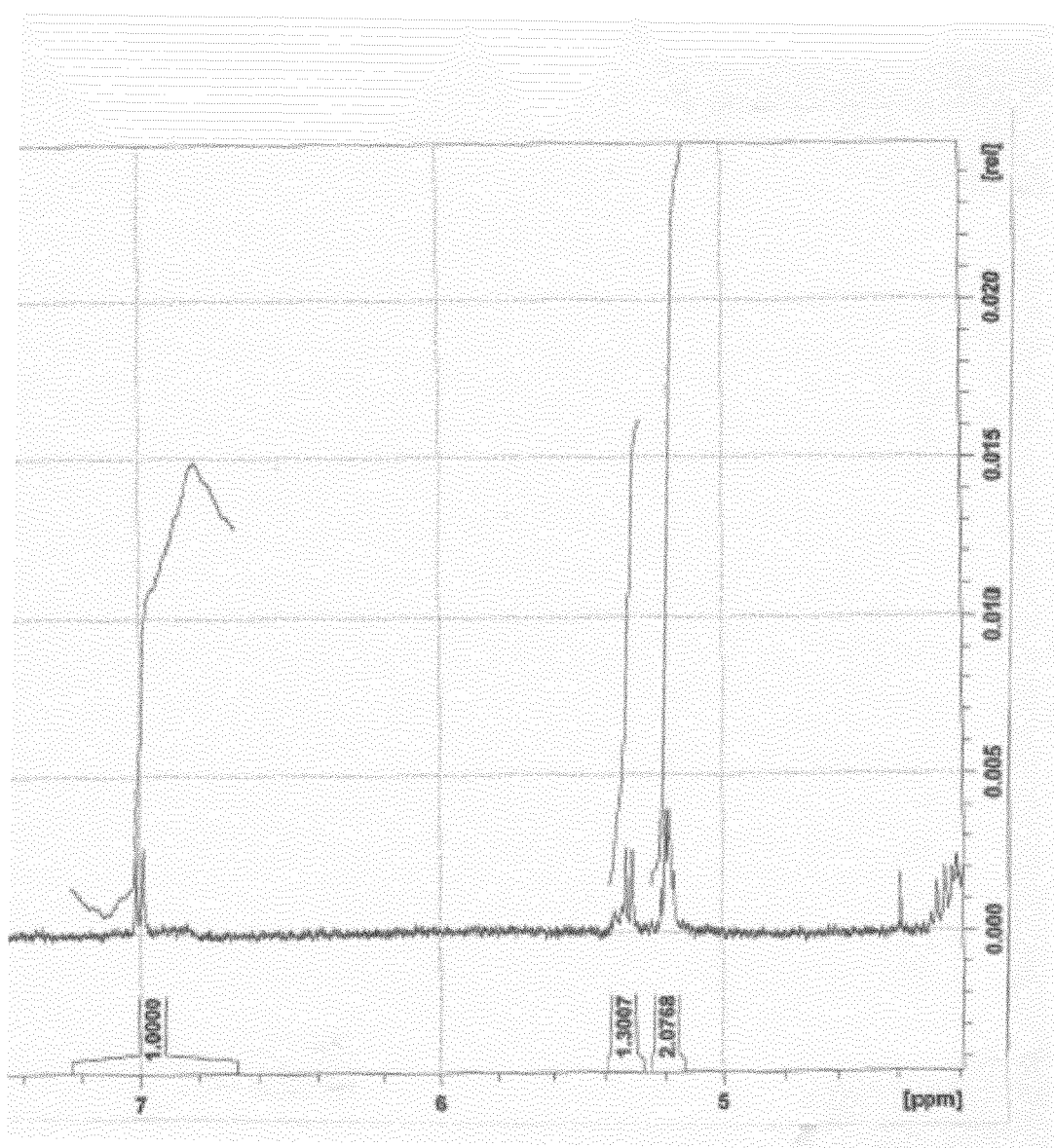
FIG. 18 displays the $^1$H NMR spectrum of the vinylic protons of compound MH$^+$=1005.58917.

With respect to compound B, in the $^1$H NMR spectrum (FIG. 18), the multiplet at 5.18 ppm corresponds to the two ethylenic protons of the fatty acid chain. The chemical shift and the multiplicity of the signal indicate that the two protons are not conjugated with the carbonyl function.

After full hydrolysis and derivatisation by Marfey's reagent in standard conditions, the amino acids Ala, Leu, Gln, Ser were identified as having the L configuration by LC/MS comparison with standards.

Example of Pharmaceutical Compositions

1/ A pharmaceutical composition for injection was prepared containing:
Compound A: 500 mg
Sterile aqueous excipient q.s.f. 5 cm$^3$ 2/ A pharmaceutical composition for injection was prepared containing:
Compound C: 2 g
Sterile aqueous excipient q.s.f. 5 cm$^3$ Antibacterial Activities of the Compounds The measures of activities were conducted on molecules 978 (A), 1004 (B) and 1006 (C), following the protocol recommended by the Clinical and Laboratory Standards Institute (CLSI)—Clinical and Laboratory Standards Institute (CLSI, formerly NCCLS):

1. Methods for Dilution Antibacterial Susceptibility Tests for Bacteria That Grow Aerobically; Approved Standard—Tenth Edition (2015). Clinical and Laboratory Standards Institute Document M07-A10.
2. Methods for Antimicrobial Susceptibility Testing of Anaerobic Bacteria; Approved Standard—Eighth Edition (2012). Clinical and Laboratory Standards Institute Document M11-A8.
3. Antimycobacterial activity was determined as described in Journal of Clinical Microbiology (2009, 47:1773-1780) by Springer et al. Quantitative drug susceptibility testing of *Mycobacterium tuberculosis* by use of MGIT 960 and EpiCenter Instrumentation.

The activities are illustrated in tables 2 and 3 hereafter.

TABLE 2

| | Minimal Inhibitory Concentration (MIC) µg/mL | | |
|---|---|---|---|
| Strain | A | B | C |
| *S. aureus* - ATCC 13709 (Fully susceptible) | ≤0.04 | ≤0.04 | ≤0.04 |
| *S. aureus* - ATCC 1683 (Methicillin resistant) | ≤0.3 | ≤0.3 | ≤0.3 |

TABLE 2-continued

| | Minimal Inhibitory Concentration (MIC) µg/mL | | |
|---|---|---|---|
| Strain | A | B | C |
| *S. pneumoniae* - ATCC 33400 | ≤0.15 | ≤0.15 | ≤0.08 |
| *S. aureus* - USA300 | ≤0.08 | ≤0.08 | ≤0.08 |

TABLE 3

Extended antibacterial activities of compound 1006 (C).

| Strain ID | Strain | Characterized Resistance | MIC (µg/mL) |
|---|---|---|---|
| Gram-positive Aerobe: | | | |
| ATCC13709 | *S. aureus* | Methicillin sensitive | ≤0.04 |
| ATCC1683 | *S. aureus* | Methicillin resistant | ≤0.3 |
| 37361192 | *S. epidermidis* | Methicillin sensitive | ≤0.25 |
| 31435861 | *S. epidermidis* | Methicillin resistant | ≤0.25 |
| 31432663 | *S. agalactiae* | | ≤0.25 |
| 37352281 | *S. pyogenes* | | ≤0.5 |
| 39050149 | *S. mitis* | | ≤0.25 |
| 39151368 | *S. oralis* | | ≤0.25 |
| R119 (R6 like) | *S. pneumoniae* | Penicillin sensitive | ≤0.125 |
| 6883 | *S. pneumoniae* | Penicillin resistant | ≤0.125 |
| ATCC1858 | *E. faecium* | Vancomycin (Van) sensitive | ≤0.5 |
| 31152980 | *E. faecium* | Van A resistant | ≤0.25 |
| 31430797 | *E. faecium* | Van B resistant | ≤0.25 |
| Gram-positive Anaerobe: | | | |
| ATCC 700057 | *C. difficile* | | ≤0.25 |
| 1201 | *P. acnes* | | ≤0.06 |
| Mycobacteria: | | | |
| H37Rv | *M. tuberculosis* | | ≤1 |

Analytical Data

| | Compound A | Compound B | Compound C |
|---|---|---|---|
| appearance | off-white powder | off-white powder | off-white powder |
| Molecular formula | $C_{45}H_{78}N_{12}O_{10}S$ | $C_{47}H_{80}N_{12}O_{10}S$ | $C_{47}H_{82}N_{12}O_{10}S$ |
| Molecular weight | 978 | 1004 | 1006 |
| HR-MS (M + H)$^+$ | 979.57340 | 1005.58917 | 1007.60472 |

TABLE 4

The NMR data of compound MH$^+$ = 979.57340 in CD$_3$CN/D$_2$O, (chemical shifts of CD$_3$CN are taken as references, $^1$H: 1.97 ppm, $^{13}$C: 0.47 ppm)

| | | | CH$_2$NH | CH$_3$NH | CH$_2$CO | 2*CH$_2$ | | 10CH$_2$ | | C=O | NH—C=N |
|---|---|---|---|---|---|---|---|---|---|---|---|
| Fatty acid chain | | $^1$H | 3.08 | 2.74 | 2.16 | 1.51 | 1.51 | 1.27 | 1.24 | | |
| | | $^{13}$C | 41.1 | 27.3 | 35.6 | 25.3 | 28.3 | 26.1 | 29.0 | 175.0 | 155.6 |
| | | | | | N—CH=C<u>H</u>—S | | | N—C<u>H</u>=CH—S | | | | |
| Aminovinylthio group | | $^1$H | | | 5.52 (J = 6.9 Hz) | | | 7.21 (J = 6.9 Hz) | | | |
| | | $^{13}$C | | | 99.2 | | | 132.5 | | | | |

TABLE 4-continued

The NMR data of compound MH⁺ = 979.57340 in CD$_3$CN/D$_2$O, (chemical shifts of CD$_3$CN are taken as references, $^1$H: 1.97 ppm, $^{13}$C: 0.47 ppm)

| Residu | | C☐H | C☐H | C☐H | C☐H | C=O | CONH$_2$ |
|---|---|---|---|---|---|---|---|
| Ala | $^1$H | 4.45 | 1.29 | | | | |
| | $^{13}$C | 48.8 | 16.5 | | | 172.8 | |
| Leu | $^1$H | 3.82 | 1.71-1.49 | 1.51 | 0.86 | 0.83 | |
| | $^{13}$C | 50.5 | 37.9 | 23.7 | 22.8 | 20.6 | 174.5 |
| Gly | $^1$H | 3.84-3.77 | | | | | |
| | $^{13}$C | 45.7 | | | | 171.5 | |
| Ser | $^1$H | 4.15 | 3.94-3.87 | | | | |
| | $^{13}$C | 55.5 | 59.1 | | | 168.0 | |
| AviCys | $^1$H | | 3.51-2.42 | 5.52 | 7.21 | | |
| | $^{13}$C | Cq 60.7 | 40.6 | | | 172 | |
| Gln | $^1$H | 4.41 | 1.94-1.83 | 2.16 | | | |
| | $^{13}$C | 53.0 | 25.6 | 30.7 | | 172.7 | 177.1 |

TABLE 5

NMR data of compound MH⁺ = 979.57340 in CD$_3$CN/D$_2$O with 0.2% CD$_3$COOD

| Residue | Atom ($^1$H) | δ ($^1$H) | Atom ($^{13}$C) | δ ($^{13}$C) |
|---|---|---|---|---|
| Fa0 | H19 | 2.74 | C19 | 27.4 |
| | H18 | 6.64 | — | — |
| | — | — | C17 | 155.8 |
| | H16 | 6.47 | — | — |
| | H15 | 3.08 | C15 | 41.3 |
| | H14 | 1.51 | C14 | 28.3 |
| | H13 | 1.27 | C13 | 26.2 |
| | H4-12 | 1.22 | C4-C12 | 29.1 |
| | H3 | 1.50 | C3 | 25.3 |
| | H2 | 2.17 | C2 | 35.6 |
| | — | — | C1 | 175.0 |
| Ala1 | H$_N$ | 7.71 | — | — |
| | Hα | 4.63 | Cα | 48.8 |
| | Hβ | 1.30 | Cβ | 16.9 |
| | — | — | C' | 172.7 |
| DhySer2 | H$_N$ | 7.88 | — | — |
| | Hα | 4.55 | Cα | 49.7 |
| | Hβ' | 2.67 | Cβ | 28.5 |
| | Hβ" | 2.33 | — | — |
| | — | — | C' | 170.7 |
| Leu3 | H$_N$ | 8.51 | — | — |
| | Hα | 3.86 | Cα | 50.6 |
| | Hβ' | 1.70 | Cβ | 38.1 |
| | Hβ" | 1.50 | — | — |
| | Hγ | 1.50 | Cγ | 23.8 |
| | Hδ' | 0.84 | Cδ' | 20.7 |
| | Hδ" | 0.85 | Cδ" | 22.9 |
| | — | — | C' | 174.9 |
| Gly4 | H$_N$ | 7.30 | — | — |
| | Hα' | 3.86 | Cα | 45.9 |
| | Hα" | 3.82 | — | — |
| | — | — | C' | 171.5 |
| DhySer5 | H$_N$ | 7.43 | — | — |
| | | | Cα | 60.7 |
| | Hβ' | 3.57 | Cβ | 40.7 |
| | Hβ" | 2.49 | — | — |
| | — | — | C' | 172.1 |
| Gln6 | H$_N$ | 7.94 | — | — |
| | Hα | 4.46 | Cα | 53.0 |
| | Hβ' | 1.95 | Cβ | 25.9 |
| | Hβ" | 1.83 | — | — |
| | Hγ | 2.17 | Cγ | 30.9 |
| | — | — | Cδ | 177.3 |
| | Hε' | 7.21 | — | — |
| | Hε" | 6.54 | — | — |
| | — | — | C' | 172.8 |
| Ser7 | H$_N$ | 8.66 | — | — |
| | Hα | 4.15 | Cα | 55.8 |
| | Hβ' | 3.94 | Cβ | 59.2 |
| | Hβ" | 3.89 | — | — |
| | — | — | C' | 168.2 |
| dCys8 | H$_N$ | 8.78 | — | — |
| | Hα | 7.16* | Cα | 132.7 |
| | Hβ | 5.47* | Cβ | 99.5 |

Figure 10:
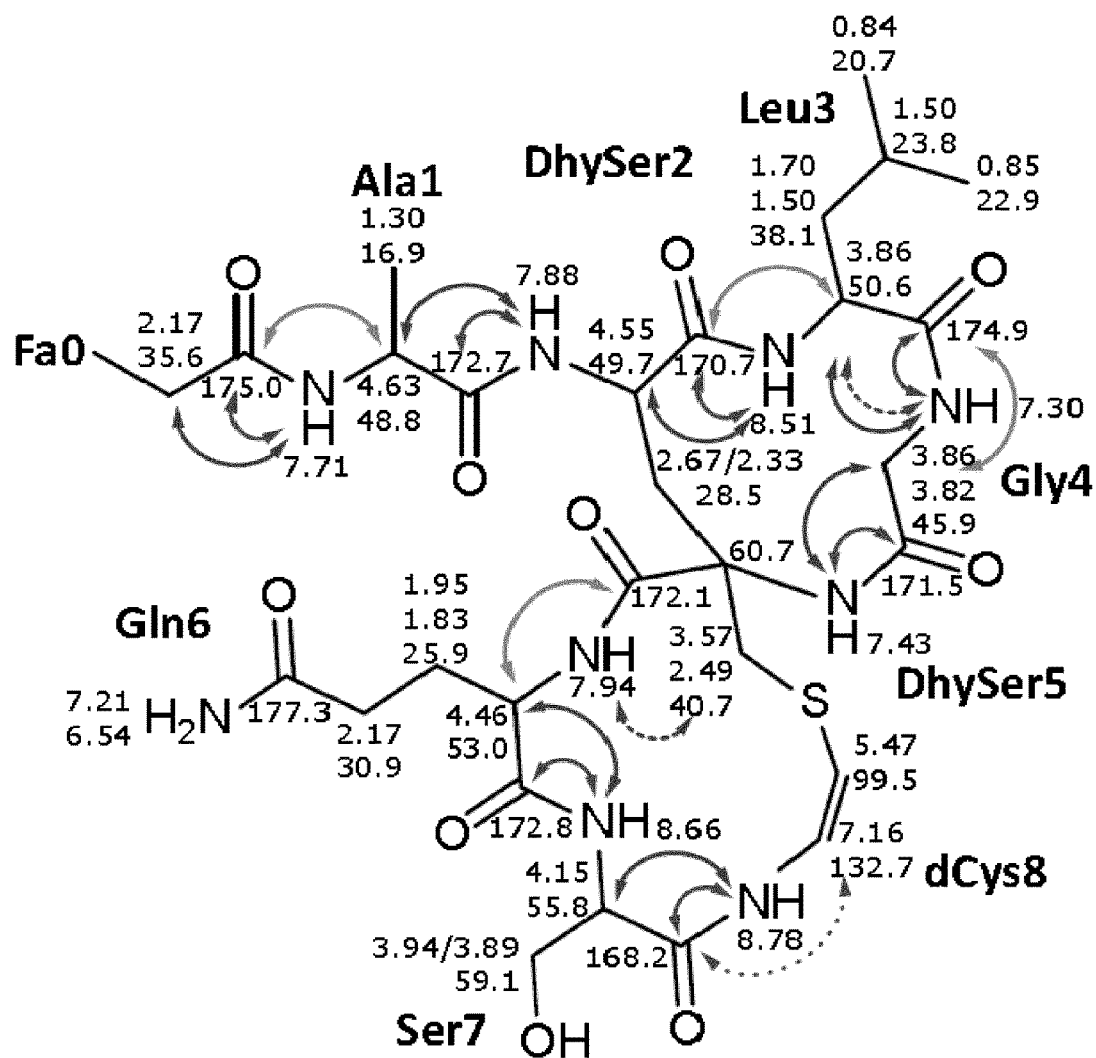
FIG. 10 displays a consistent picture of the sequential arrangement of building blocks in compound MH$^+$=979.57340.

Fa - bismethylguanidine pentadecanaic acid,
DhySer—dehydroxyserine,
dCys—decarboxylated vinyl cysteine *$^3$/$_{HH}$ approx. 7.3 Hz Inter-residual NOE contacts between HNi and Hαi-1 yielded a consistent picture of the sequential arrangement of building blocks in compound MH⁺=979.57340 (FIG. 10).

Figure 11:
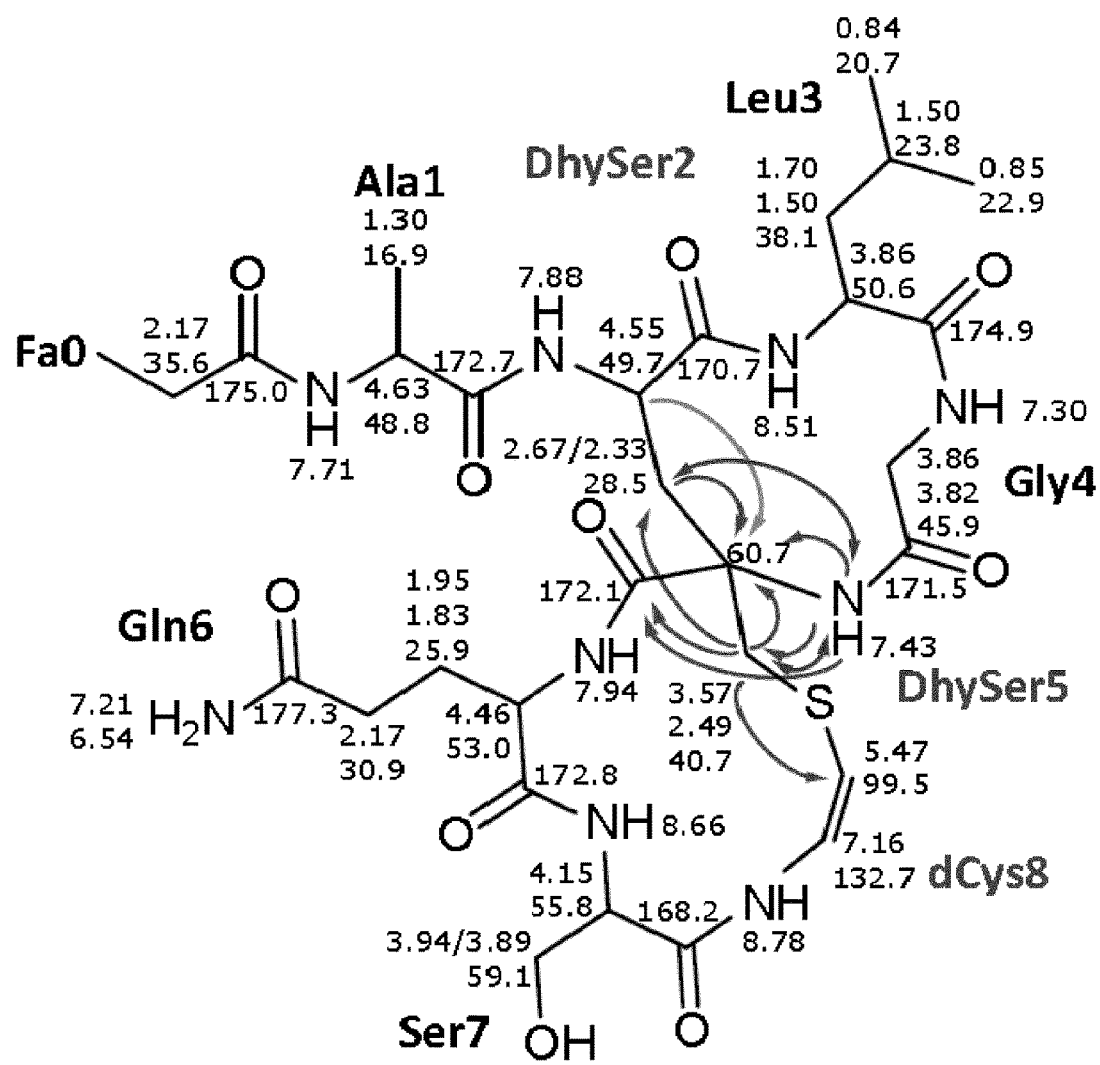
FIG. 11 summarizes the inter-residual correlations that unambiguously define the bicyclic lantipeptide system in compound 979.57340.
Figure 12:
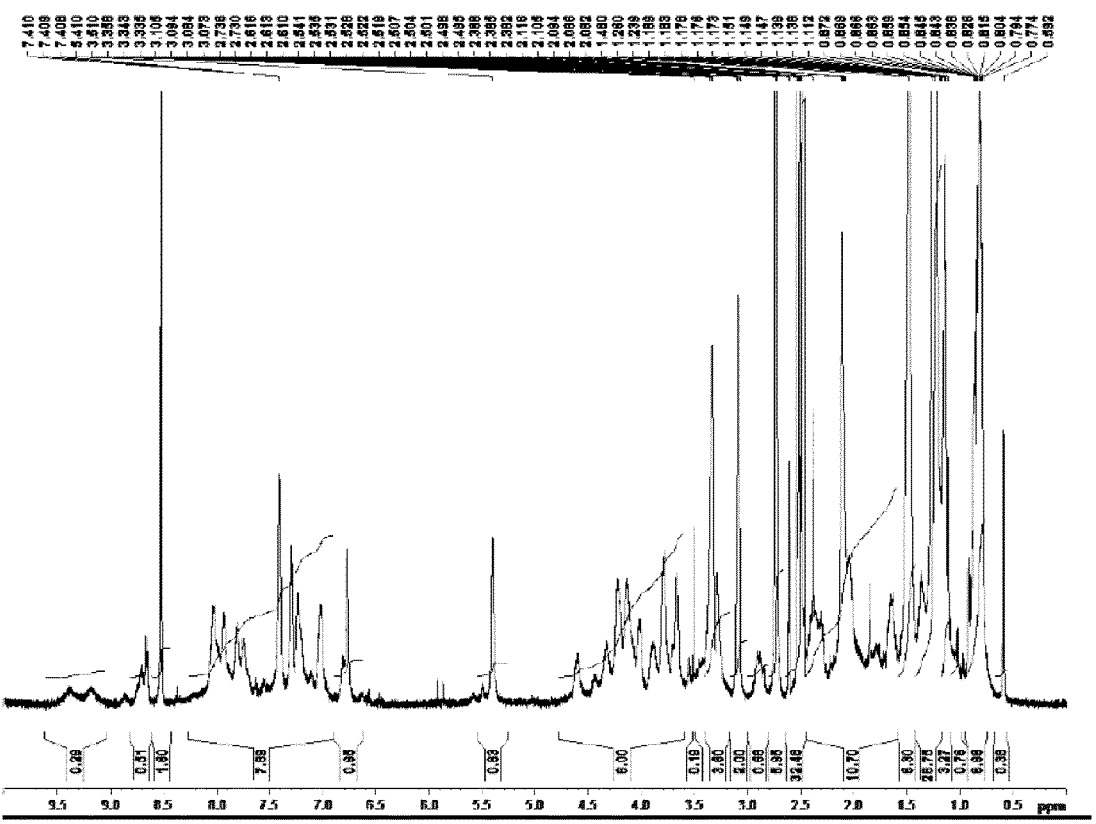
FIG. 12 displays the 1H NMR spectrum of compound MH$^+$=1007.60472 (600 MHz, DMSO-d6, 300K).
Figure 13:
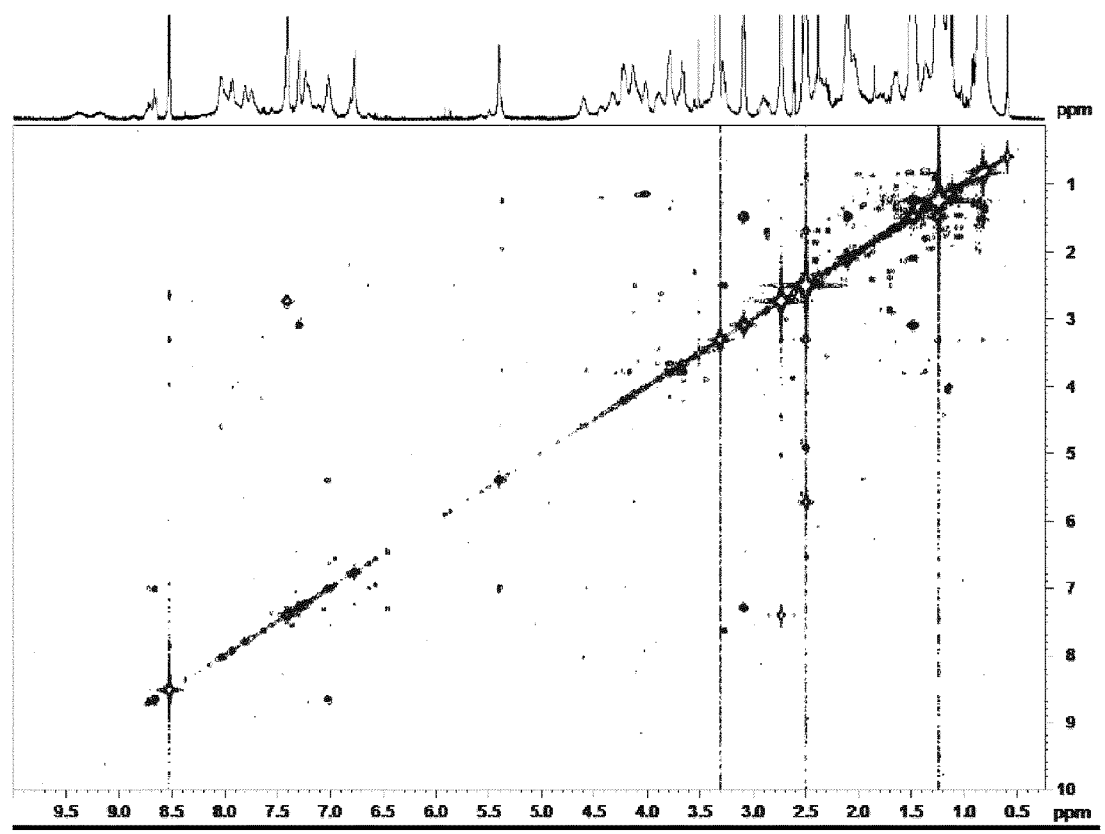
FIG. 13 displays the 1H-1H COSY NMR spectrum of compound MH$^+$=1007.60472 (600 MHz, DMSO-d6, 300K).
Figure 14:
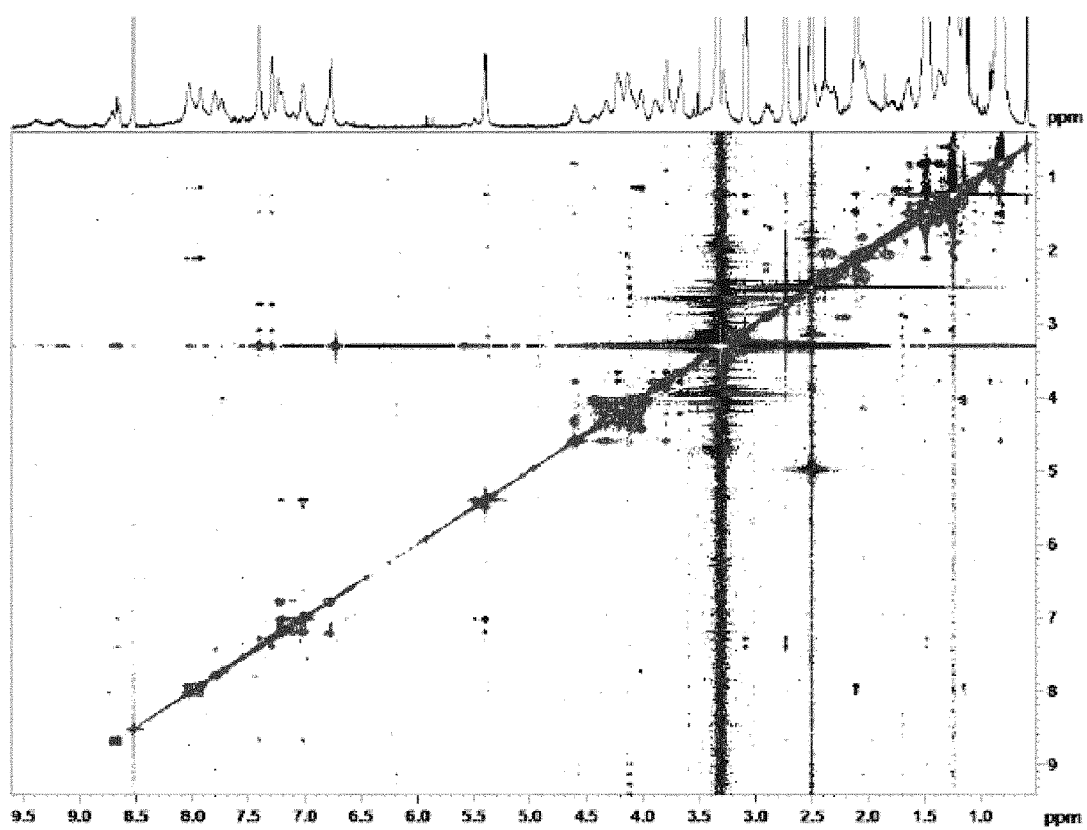
FIG. 14 displays the ROSY NMR spectrum of compound MH$^+$=1007.60472 (600 MHz, DMSO-d6, 300K).
Figure 15:
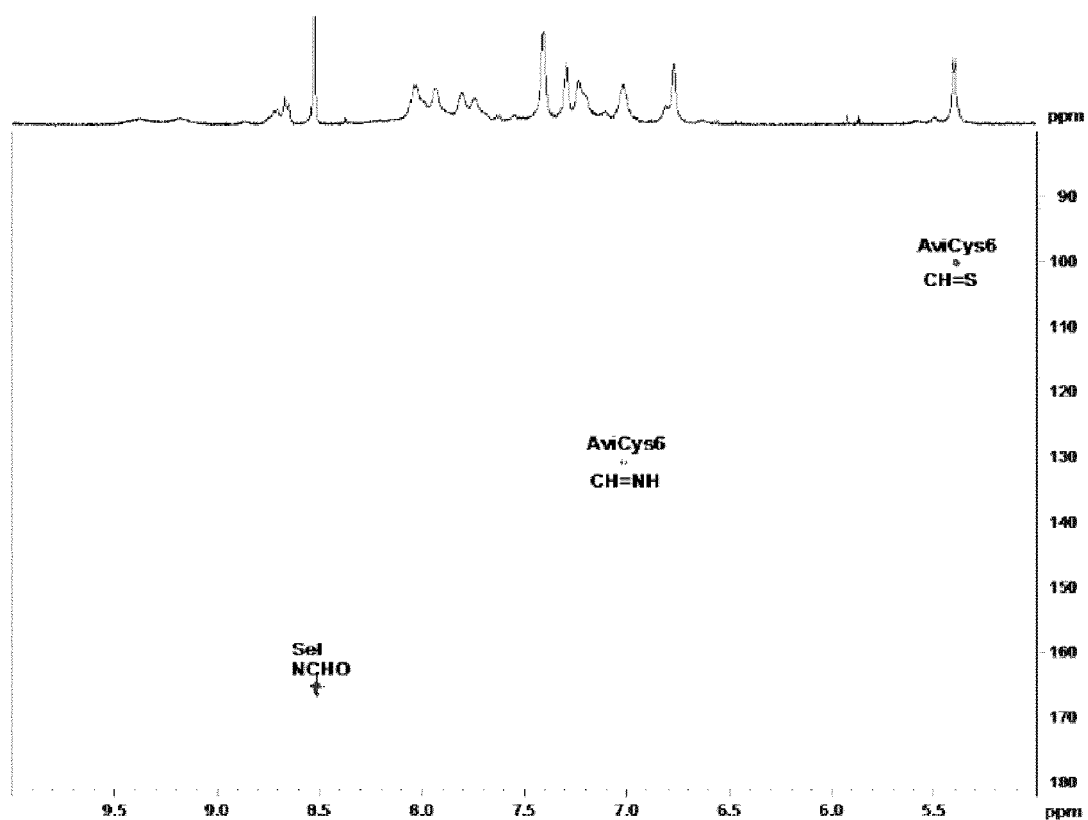
FIG. 15 displays the C-edited HSQC spectrum (from 5.0 to 10 ppm) of compound 1007.60472 (600 MHz, DMSO-d6, 300K) containing the aminovinylthio group.
Figure 16:
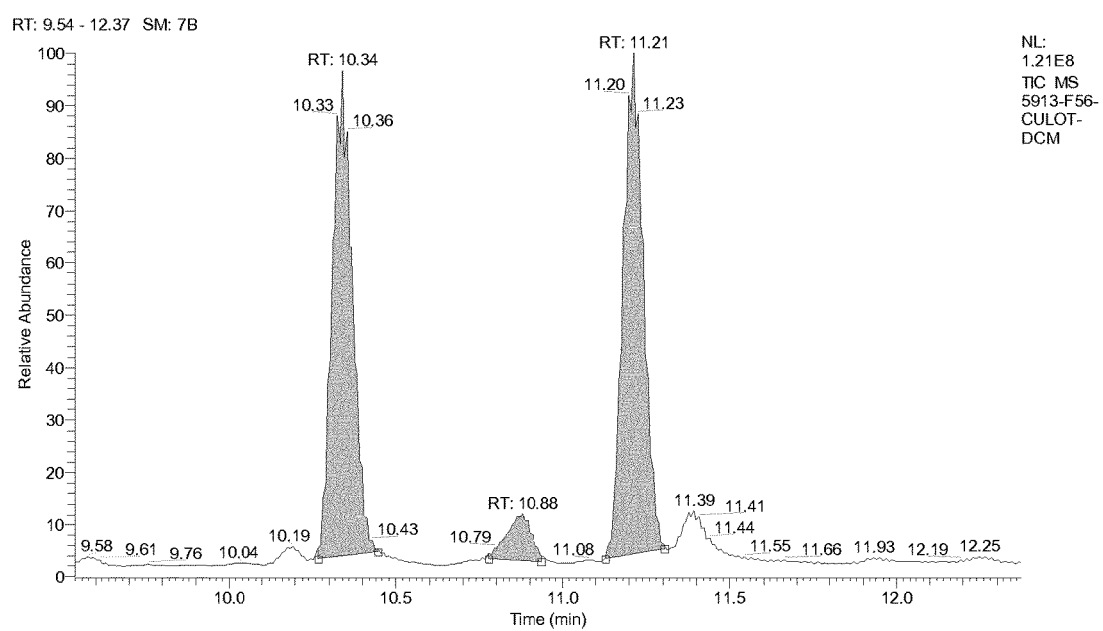
FIG. 16 displays the HPLC-HRMS of compounds MH+=979.57340 (A), MH$^+$=1005.58912 (B), MH$^+$=1007.60472 (C).
Figure 17:
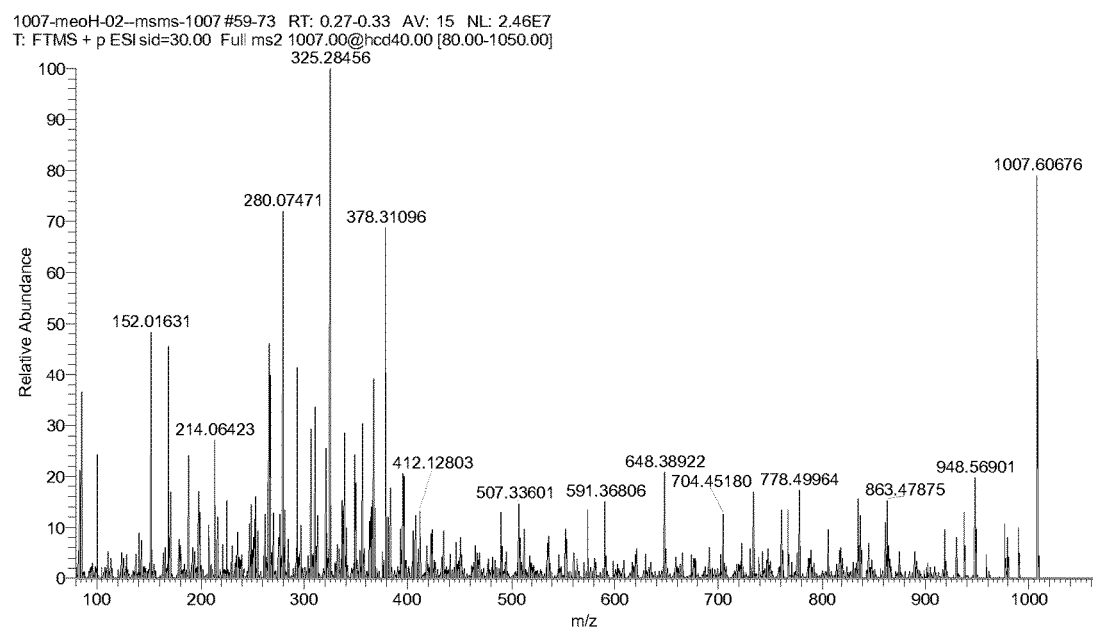
FIG. 17 displays the ESI-LIT-Orbitrap of compound MH$^+$=1007.60472.

FIG. 11 summarizes the inter-residual correlations that unambiguously define the lantipeptide bicyclic system.

TABLE 6

The NMR data of compound 1007.60472 in DMSO-d$_6$, (chemical shifts of DMSO are taken as references, $^1$H: 2.50 ppm, $^{13}$C: 39.52 ppm)

| | | NH | CH$_2$NH | CH$_3$NH | CH$_2$CO | 2*CH$_2$ | 12CH$_2$ | C=O | NH—C=N |
|---|---|---|---|---|---|---|---|---|---|
| Fatty acid chain | $^1$H | 7.40 7.29 | 3.09 | 2.73 | 2.10 | 1.48 1.48 | 1.26 1.24 | | |
| | $^{13}$C | | 40.7 | 27.7 | 34.8 | 24.9 28.2 | 25.8 28.8 | 172.1 | 155.1 |

| | | N—CH=CH—S | | N—CH=CH—S | |
|---|---|---|---|---|---|
| Aminovinylthio group | $^1$H | 5.40 ($^3$J = 6.9 Hz) | | 7.02 ($^3$J = 6.9 Hz) | |
| | $^{13}$C | 101.0 | | 131.7 | |

TABLE 6-continued

The NMR data of compound 1007.60472 in DMSO-d$_6$, (chemical shifts of DMSO are taken as references, $^1$H: 2.50 ppm, $^{13}$C: 39.52 ppm)

| Residu | | NH | C☐H | C☐H | C☐H | C☐H | other |
|---|---|---|---|---|---|---|---|
| Ala | $^1$H | 7.94 | 4.02 | 1.14 | | | |
| | $^{13}$C | | 48.8 | 17.1 | | | |
| Leu | $^1$H | 8.04 | 4.60 | 1.49-1.25 | 1.51 | 0.82   0.80 | |
| | $^{13}$C | | | 40.4 | 24.2 | 22.0   22.9 | |
| Gly | $^1$H | 7.80 | 3.90-3.45 | | | | |
| | $^{13}$C | | 43.8 | | | | |
| Ser | $^1$H | | 4.23 | 3.79-3.68 | | | OH 5.57 |
| | $^{13}$C | | 56.4 | 60.1 | | | |
| AviCys | $^1$H | 8.65 | | 3.76-2.88 | 5.40 | 7.02 | |
| | $^{13}$C | | | 41.9 | 101.0 | 131.7 | |
| Gln | $^1$H | | 4.15 | 2.09-2.03 | 2.40-2.34 | | NH$_2$ 6.78-7.25 |
| | $^{13}$C | | 56.2 | 26.1 | 31.2 | | |

HPLC Column
  Phenomenex Gemini NX, 5μ, C18, 110 Å, 150×2 mm
UPLC/"Orbitrap Technology", Exactive, Thermo Fisher Scientific
HESI Probe
MS High Resolution (Exact Mass+/−5 ppm)

| | |
|---|---|
| Sheath Gas | 25 |
| Aux Gas | 5 |
| Spray Voltage (+) | 3000 |
| Capillary Temperature | 250 |
| Capillary Voltage (V) | 95 |
| Tube lens voltage (V) | 180 |
| Skimmer voltage (V) | 28 |
| Capillary Voltage (V) | 95 |
| Heater Temperature | 350 |
| 2 scans (amu) | 200-600 |
| | 450-1600 |

UPLC Accela AS Method

| | |
|---|---|
| Injection volume (μl) | 20 |
| Flush volume(μl) | 2000 |
| Needle height from bottom(mm) | 2 |
| Wash volume (μl) | 2000 |
| Flush speed (μl/s) | 100 |
| Syringe speed (μl/s) | 8 |
| Injection mode is no waste | |
| Loop loading speed (μl/s) | 8 |
| Tray temp control is off | |
| Column oven control is on. Temp © | 26 |

Divert Valve

| | |
|---|---|
| Switch1 (waste) | 0-2 min |
| Switch 2 (MS) | 2-15 min |
| Switchn 1 (waste) | 15-18 min |

Pump Method

| Time (min) | ACN + 0.1% Acide Formique (%) | H$_2$O (%) | Flow (μl/min) |
|---|---|---|---|
| 0 | 0 | 100 | 500 |
| 2 | 0 | 100 | 500 |
| 13 | 50 | 50 | 500 |
| 15 | 50 | 50 | 500 |
| 18 | 0 | 100 | 500 |

TABLE 7

HRMS of compounds MH$^+$ 979.57340 (A), MH$^+$ 1005.58912 (B), MH$^+$ 1007.60472 (C)

| | | Compound A | | Compound B | | Compound C | |
|---|---|---|---|---|---|---|---|
| | | MH+ | (M2H)2+ | MH+ | (M2H)2+ | MH+ | (M2H)2+ |
| ESI-HRMS | Mean | 979.57340 | 490.29 | 1005.58917 | 503.29826 | 1007.60472 | 504.30607 |
| | Std error | 0.00188 | 0.00090 | 0.00196 | 0.00091 | 0.00197 | 0.00097 |
| | CV % | 0.00019 | 0.00018 | 0.00019 | 0.00018 | 0.00019 | 0.00019 |
| | N | 27 | 23 | 26 | 21 | 26 | 22 |

| Overall Status: | |
|---|---|
| Status: | Instrument status Ok |
| Performance: | Ok |
| Ion Source: | |
| Spray Voltage (V) | 3000.9 |
| Spray Current (μA) | 0.91 |
| Capillary Temperature (° C.) | 249.91 |
| Sheath gas flow rate | 5.51 |
| Aux gas flow rate | 0.05 |
| Sweep gas flow rate | 0.10 |
| Aux. Temperature (° C.) | 40.28 |
| Ion Optics: | |
| Capillary Voltage (V) | −0.4 |
| Bent Flatapole DC (V) | 6.1 |
| Inj Flatapole DC (V) | 8.1 |
| Trans Multipole DC (V) | 3.9 |
| HCD Multipole DC (V) | −73.7 |
| RF0 and RF1 Amp (V) | 753.7 |
| RF0 and RF1 Freq (kHz) | 3309.000 |
| RF2 and RF3 Amp (V) | 596.4 |
| RF2 and RF3 Freq (kHz) | 2802.000 |
| Inter Flatapole DC (V) | 6.97 |
| Quad Exit DC (V) | −28.18 |
| C-Trap Entrance Lens DC (V) | 6.10 |
| C-Trap RF Amp (V) | 1010.0 |
| C-Trap RF Freq (kHz) | 3.198 |
| C-Trap RF Curr (A) | 0.122 |
| C-Trap Exit Lens DC (V) | −55.15 |
| HCD Exit Lens DC (V) | 34.73 |
| Vacuum: | |
| Fore Vacuum Sensor (mbar) | 1.63 |
| High Vacuum Sensor (mbar) | 3.18e−09 |
| UHV Sensor (mbar) | 2.41e−10 |
| Source TMP Speed | 1000.0 |
| UHV TMP Speed | 1000.0 |
| Temperatures: | |
| Analyzer Temperature (° C.) | 29.21 |
| Ambient Temperature (° C.) | 24.6 |
| Ambient Humidity (%) | 0.0 |
| Source TMP Motor Temperature | 57.0 |
| Source TMP Bottom Temperature | 47.0 |
| UHV TMP Motor Temperature (° C.) | 36.0 |
| IOS Heatsink Temp. (° C.) | 31.3 |
| HVPS Peltier Temp. (° C.) | 34.92 |
| Quad. Det. Temp. (° C.) | 38.25 |
| Diagnostic Data: | |
| Performance ld | 120.752 |
| Performance me | 1052.953 |
| Performance cy: | 1.975 |
| CTCD mV | −0.75 |

TABLE 8

Results for ESI-LIT-Orbitrap of compounds MH⁺ 979.57340 (pic 1), MH⁺ 1007.60472 (pic 3)

| m/z | | Delta |
|---|---|---|
| 1007.60352 | 979.57233 | 28.03119 |
| 989.59393 | 961.56256 | 28.03137 |
| 976.56238 | 948.53113 | 28.03125 |
| 948.56757 | 920.53607 | 28.03150 |
| 937.55078 | 909.51984 | 28.03094 |
| 863.47791 | 835.44641 | 28.03150 |
| 837.49878 | 809.46765 | 28.03113 |
| 806.45593 | 778.42505 | 28.03088 |
| 789.42810 | 761.39996 | 28.02814 |
| 778.49786 | 750.46753 | 28.03033 |
| 761.47223 | 733.44067 | 28.03156 |
| 733.47693 | 705.44586 | 28.03107 |
| 722.46161 | 694.43048 | 28.03113 |
| 705.43365 | 677.40369 | 28.02996 |

TABLE 8-continued

Results for ESI-LIT-Orbitrap of compounds MH⁺ 979.57340 (pic 1), MH⁺ 1007.60472 (pic 3)

| m/z | | Delta |
|---|---|---|
| 691.52075 | 663.48975 | 28.03100 |
| 648.38806 | 620.35712 | 28.03094 |
| 378.31021 | 350.27905 | 28.03116 |
| 325.28378 | 297.25269 | 28.03109 |

The invention claimed is:

1. A bicyclic lipolantipeptide comprising (i) the amino acids Ala, Gln, Leu and Ser, each being of the L-configuration, and Gly; (ii) an aminovinylthio group; and (iii) a saturated or unsaturated linear fatty acid chain substituent, the terminal carbon of the fatty acid chain carrying a guanidine group optionally substituted by one or two ($C_1$-$C_6$) alkyl groups, and any acid salt thereof, wherein said bicyclic lipolantipeptide is selected from:

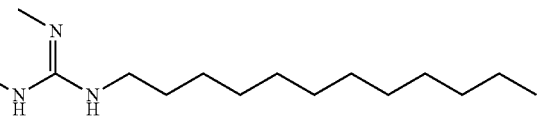

formula A

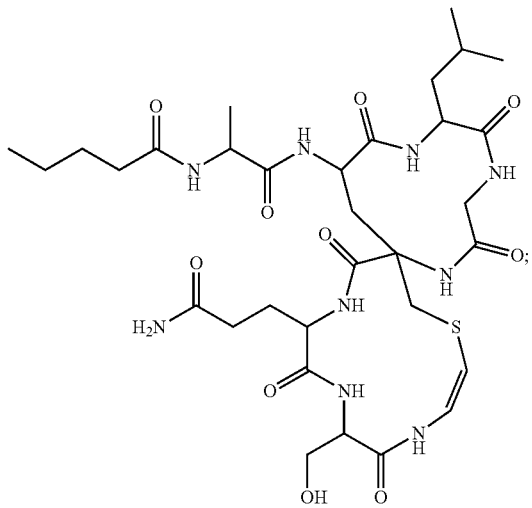

formula C
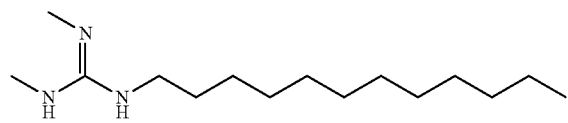
formula B
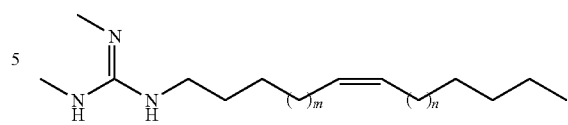
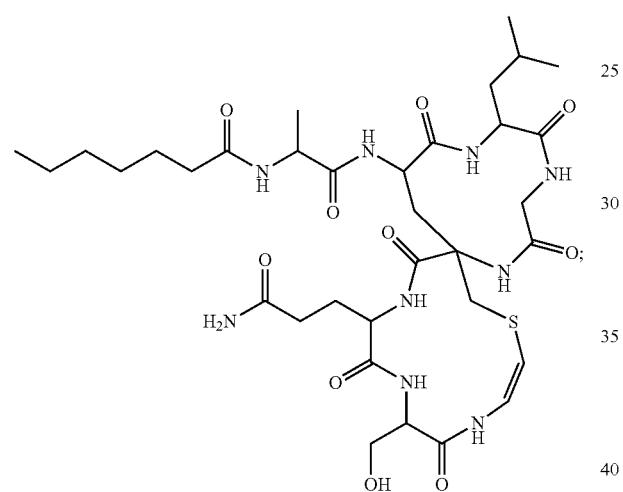
or
( )m and ( )n representing a total of 7 CH$_2$ groups.
2. The bicyclic lipolantipeptide according to claim 1, said lipolantipeptide having formula A:
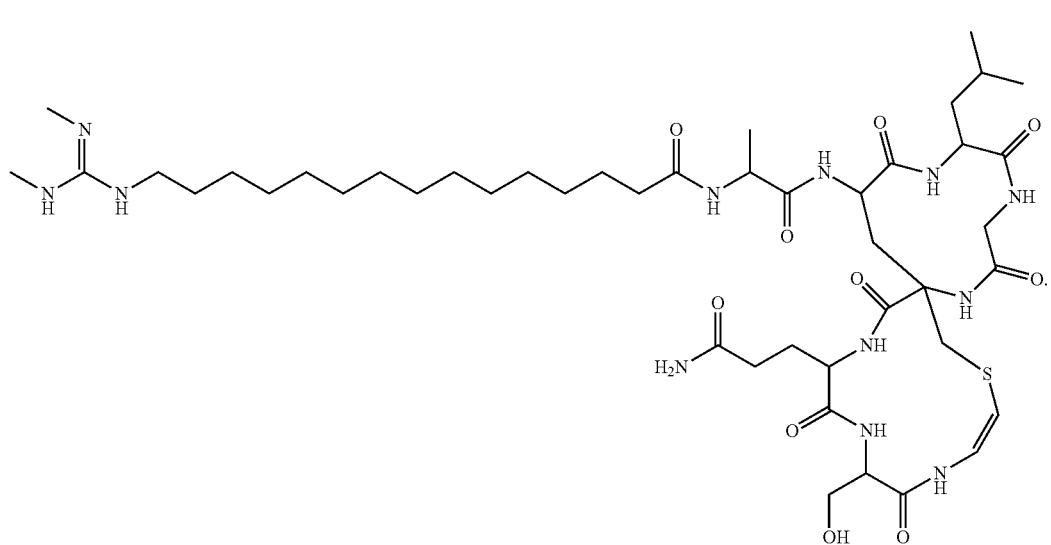

3. The bicyclic lipolantipeptide according to claim 1, said lipolantipeptide having formula C:

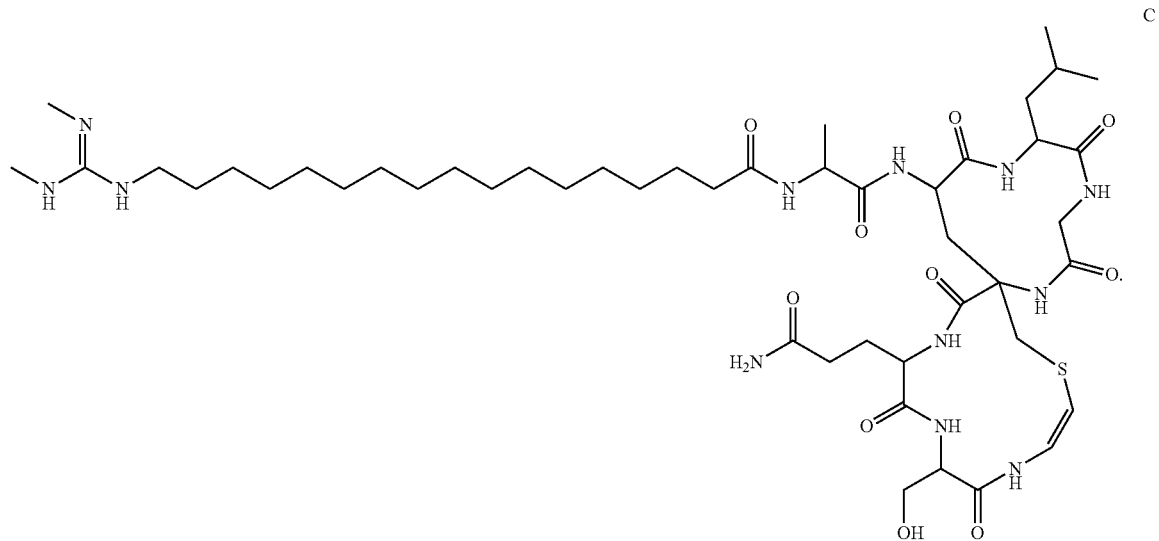 [SMILES: C/N=C(\NC)NCCCCCCCCCCCCCCCCC(=O)NC(C)C(=O)NC1CC2(CS/C=C\NC(=O)C(CO)NC(=O)C(CCC(N)=O)NC2=O)NC(=O)CNC(=O)C(CC(C)C)NC1=O]

4. The bicyclic lipolantipeptide according to claim 1, said lipolantipeptide having formula B:

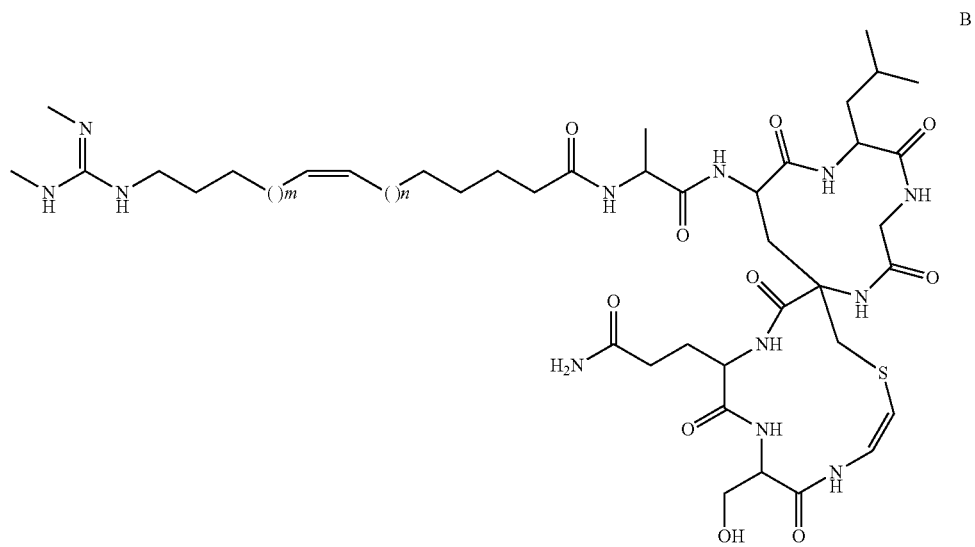

( )m and ( )n representing a total of 7 CH$_2$ groups.

5. A method of treating a microbial infection in a human, animal, or plant comprising the administration of a bicyclic lipolantipeptide according to claim 1 to a human, animal or plant having a microbial infection.

6. A pharmaceutical composition comprising a bicyclic lipolantipeptide according to claim 1, or a pharmaceutically acceptable salt thereof, and, if appropriate, a pharmaceutically acceptable carrier and/or excipient.

7. A method for treating plants against pathogen infection comprising exposing a plant to an effective amount of a bicyclic lipolantipeptide according to claim 1 or an addition salt thereof.

8. A phytosanitary composition comprising a bicyclic lipolantipeptide according to claim 1, or an acceptable salt thereof and, if appropriate, an acceptable carrier and/or excipient.

* * * * *